United States Patent [19]

Halskov

[11] Patent Number: 5,629,012
[45] Date of Patent: May 13, 1997

[54] PROCESS FOR PRODUCING SUPPOSITORIES BY COMPRESSION AND SUPPOSITORIES OBTAINED BY THE PROCESS

[75] Inventor: Søren Halskov, Virum, Denmark

[73] Assignee: Farmaceutisk Laboratorium Ferring A/S, Vanlose, Denmark

[21] Appl. No.: 450,884

[22] Filed: May 26, 1995

Related U.S. Application Data

[63] Continuation of Ser. No. 167,818, filed as PCT/DK92/00187 Jun. 16, 1992, published as WO92/22283 Dec. 23, 1992, abandoned.

[30] Foreign Application Priority Data

Jun. 17, 1991 [DK] Denmark ................................ 1165/91

[51] Int. Cl.⁶ ........................................................ A61K 9/02
[52] U.S. Cl. ................... 424/436; 424/DIG. 15; 514/966; 514/967; 514/968
[58] Field of Search ............................ 424/436, 484, 424/DIG. 15; 514/966, 967, 968

[56] References Cited

U.S. PATENT DOCUMENTS 3,849,549  11/1974  Dempski et al. ........................ 424/436

FOREIGN PATENT DOCUMENTS

| 0111137 | 6/1984 | European Pat. Off. . | |
| 2248777 | 6/1972 | Germany . | |
| 0004078 | 2/1970 | Japan | 424/436 |
| 0157820 | 5/1978 | Japan | 424/436 |
| 0002080 | of 1880 | United Kingdom | 424/436 |

OTHER PUBLICATIONS

Gennaro, A. R. (1985). Remington's Pharmaceutical Sciences. Mack Pub. Co., pp. 1580–1584.

*Primary Examiner*—Raj Bawa
*Attorney, Agent, or Firm*—Jacobson, Price, Holman & Stern, PLLC

[57] ABSTRACT

Suppositories, produced by a process in which a suppository basic mass is produced containing (a) 50–75% of 5-aminosalicylic acid as an active ingredient, (b) 2–5% talc, magnesium stearate and/or polyvinyl pyrrolidone and (c) 20–48% by weight of a polyethylene glycol having an average molecular weight of at least 4000, and the produced mass is compressed to suppositories in a tabletting machine.

3 Claims, No Drawings

PROCESS FOR PRODUCING SUPPOSITORIES BY COMPRESSION AND SUPPOSITORIES OBTAINED BY THE PROCESS

This application is a continuation of application Ser. No. 08/167,818, filed as PCT/DK92/00187 Jun. 16, 1992, published as WO92/22283 Dec. 23, 1992, now abandoned.

BACKGROUND OF THE INVENTION

1. Field of the Invention

The present invention concerns a special process for producing suppositories by compression, and the process of the invention is characterized by producing a suppository mixture granulate containing a considerably greater amount of active drug than ordinary suppositories as well as 20–50% by weight of a polyethylene glycol having an average molecular weight of at least 4000, and producing the suppositories in the same manner as tablets, i.e. by compression, instead of by moulding. The invention moreover concerns the suppositories obtained by the process which have a considerably higher percentual content of active drug than ordinary suppositories.

2. Description of the Prior Art

As will be known, suppositories are drugs intended for insertion into the rectum. They contain the active drug in a dosed amount and are produced by pressing, moulding or compression. They can also be produced in the form of capsules for controlled release of the active substance.

Ordinarily suppositories are produced by moulding, the produced mass being melted using the least possible amount of heat, and then the liquid mass is poured into moulds having the desired nominal capacity.

The suppositories produced by moulding are oblong and smooth, and they have a uniform appearance. Melting is intended to provide a uniform distribution of the drug in the basic mass, which, however, can be difficult to obtain because of sedimentation during hardening.

However, traditional moulding is a time-consuming and slow process which involves considerable costs. Moulded suppositories also have the drawback that too strong heating of certain suppository basic masses result in unstable modifications with a considerably reduced solidification point.

It is well-known to use polyethylene glycols having average molecular weights of 4000–6000 or above as the main component in the basic mass for suppositories produced by traditional melting and moulding. Thus, the DE Offenle-gungsschrift 2 248 777 describes melt-moulded indomethacin suppositories whose basic mass contains such polyethylene glycols.

It has previously been attempted to produce suppositories by compression or pressing, i.e. by traditional tabletting methods. However, these suppositories tend to form irregular rough surfaces, which makes them unpleasant to use for the patient. Moreover, in such a production method it has been found impossible to dose the drug in so high doses as is often desirable owing to the prescribed treatment.

Thus, the EP publication 111 137 describes suppositories containing the drug indomethacin in a base consisting of polyethylene glycol having an average molecular weight of up to 35,000. It is stated that the content of the active drug may be up to 50% by weight, but preferably the content is 2–40% by weight and in particular 2–26% by weight. All the examples in the publication concern rectal tablets having a content of indomethacin of 2.8–5.8% by weight and rectal capsules having a content of indomethacin of 5.25–10.5% by weight, i.e. rather low concentrations. Further, the suppositories thus known contain quite high amounts of polyethylene glycols, typically 1600–1730 mg per unit, which is a drawback, because it has been found that a content of polyethylene glycols in suppositories of 1–1.5 g per unit may cause bowel disorders.

SUMMARY OF THE INVENTION

An object of the invention is to provide a process enabling the production of suppositories having a high content of active drug, which are partly more convenient to store and are partly more convenient to use and easier and cheaper to produce than traditional melt-moulded suppositories.

It has now surprisingly been found that a composition which can easily be compressed to suppositories by an ordinary tabletting method can be obtained by using a suitable amount, more particularly 20–50% by weight, preferably 20–48% by weight, of a polyethylene glycol having an average molecular weight of at least 4000 in the suppository basic mass. The use of such a polyethylene glycol in the basic mass results in suppositories having a uniform appearance and having an extremely smooth and regular surface, which is moreover sufficiently slippery for the suppository to be inserted without difficulty. It is moreover possible in such suppositories to incorporate up to 75% by weight of active drug, which is far above normal.

DESCRIPTION OF THE PREFERRED EMBODIMENTS.

Polyethylene glycols, more particularly mixtures of condensation polymers of ethylene oxide and water, are also called "macrogols". Macrogols having average molecular weights of 200–700 are liquids, while macrogols having average molecular weights above 1000 vary in consistence from soft oily substances to hard wax-like solid substances. The average molecular weight is stated as a number after the name. "Macrogol 6000", which it is preferred to use according to the invention, thus has an average molecular weight of about 6000.

The macrogols have the general formula

where n is greater than or equal to 4. In "Macrogol 6000" n has an average value of between 158 and 204. It is a white or cream-coloured solid wax-like substance which is in the form of a powder or flakes. The melting point is 56°63° C., i.e. considerably above the body temperature. Mixtures of various polyethylene glycols having melting points above the body temperature have frequently been used as a base in suppositories from which the drug is released by dissolution.

Since the melting points of the macrogols increase with increasing average molecular weight, macrogols having high average molecular weights, such as "Macrogol 6000", have not previously been a natural choice as a suppository base material.

Mixing a granulate of the drug with "Macrogol 6000" and compressing the mixture to suppositories by a method which is known per se for the production of tablets for oral administration provide the following advantages:

1) The suppositories do not melt under normal temperature conditions, but only at about 60° C.

2) The suppositories are cheaper to produce.

3) The drug can be incorporated in very high concentrations and is considerably easier to dose uniformly.

4) The product is more convenient and more pleasant to use for the patient.

5) Avoidance of drug decomposition during the heating which is necessary in traditional moulding of suppositories.

6) It is easier to obtain and maintain a homogeneous mixture, and the risk of sedimentation is eliminated.

All active drugs which lend themselves for rectal administration may be incorporated in the suppositories produced according to the invention. One of the interesting drugs in this respect is 5-aminosalicylic acid (5-ASA), which is used particularly for the treatment of colitis ulcerosa and Crohn's disease, but which has moreover been found to be of interest for the production of suppositories for treatment of hemorrhoids. Suppositories containing 5-aminosalicylic acid are known e.g. from the EP patent application 83 775, these suppositories being produced by moulding and containing max. 500 mg of 5-aminosalicylic acid per dose unit. The suppositories of the invention may contain considerably larger amounts of 5-ASA, which is absolutely an advantage for the patient.

An example of the many active drugs which may be used is steroids for various applications.

In addition to a polyethylene glycol or a mixture of polyethylene glycols having an average molecular weight of at least 4000, preferably "Macrogol 6000", in an amount of 20–50% by weight, preferablu 20–48% by weight, the suppositories produced according to the invention contain microcrystalline cellulose and/or other additives common in the production of drugs. These additives and the active drug together amount to 45–75%, preferably 50–75%, based on the gross weight of the suppositories. Finally, the suppositories contain one or more of the substances talc, magnesium stearate and polyvinyl pyrrolidone in an amount of 2–5% by weight.

The suppositories are typically compressed to symmetrical units having an approximately elliptic longitudinal section, i.e. the two ends are uniform (in contrast to the ordinary "torpedo-shape" where one end is pointed while the other is blunt).

The following example illustrates the invention:

EXAMPLE

A suppository basic mass for the production of 1000 suppositories consists of the following ingredients:

| | |
|---|---|
| "Macrogol 6000" | 572 g |
| Microcrystalline cellulose and active drug | 1000 g |
| Magnesium stearate | 4 g |
| Talc | 4 g |
| Polyvinyl pyrrolidone + ethanol (1:19) | q.s. |

A granulate is made from the microcrystalline cellulose, the active drug, e.g. 5-aminosalicylic acid (5-ASA) and the mixture of polyvinyl pyrrolidone and ethanol.

The resulting granulate is mixed with "Macrogol 6000", and then magnesium stearate and talc are added.

The granulate can then be compressed to suppositories in a tabletting machine in a manner known per se.

I claim:

1. A suppository produced by a process comprising forming a granulate consisting essentially of (a) 50–75% of 5-aminosalicylic acid as an active ingredient, (b) 2–5% talc, magnesium stearate and polyvinyl pyrrolidone and (c) 20 4–48% by weight of a polyethylene glycol having an average molecular weight of at least 4000, and compressing the granulate to the suppository in a tabletting machine.

2. The suppository of claim 1, wherein the polyethylene glycol has an average molecular weight of 6000.

3. The suppository of claim 1, wherein the granulate is formed by mixing the polyethylene glycol with the 5-aminosalicylic acid and polyvinyl pyrrolidone and then adding the magnesium stearate and talc.

* * * * *